US005875774A

United States Patent [19]

Clementi et al.

[11] Patent Number: 5,875,774
[45] Date of Patent: Mar. 2, 1999

[54] NEBULIZER

[75] Inventors: Francis J. Clementi, Somerset; Raymond C. Hoffman, Jr., Pittsburgh, both of Pa.; Karl-Heinz Hecker, Aschau i. Ch.; Rudolf A. Schinagl, Unterhaching, both of Germany

[73] Assignee: Sunrise Medical HHG Inc., Longmont, Colo.

[21] Appl. No.: 583,278

[22] Filed: Jan. 5, 1996

[51] Int. Cl.[6] .................................................. A61M 11/00

[52] U.S. Cl. ............................... 128/200.18; 128/200.14; 128/200.21; 128/203.12; 239/338

[58] Field of Search ......................... 128/200.14, 200.18, 128/200.21, 203.12, 200.22, 200.16, 200.17, 203.15; 239/338, 120.1, 120.2

[56] References Cited

U.S. PATENT DOCUMENTS

| | | | |
|---|---|---|---|
| Re. 33,717 | 10/1991 | Svoboda | 128/200.18 |
| 3,762,409 | 10/1973 | Lester | 128/194 |
| 3,795,244 | 3/1974 | Lax et al. | 128/203.15 |
| 4,429,835 | 2/1984 | Brugger et al. | 239/338 |
| 4,512,341 | 4/1985 | Lester | 128/200.21 |
| 4,566,452 | 1/1986 | Farr | 128/200.21 |
| 4,588,129 | 5/1986 | Shanks | 239/338 |
| 4,746,067 | 5/1988 | Svoboda | 239/338 |
| 5,054,477 | 10/1991 | Terada et al. | 128/200.14 |
| 5,209,225 | 5/1993 | Glenn | 128/203.12 |
| 5,235,969 | 8/1993 | Bellm | 128/200.18 |
| 5,309,900 | 5/1994 | Knoch et al. | 128/200.14 |
| 5,312,046 | 5/1994 | Knoch et al. | 239/338 |
| 5,503,139 | 4/1996 | McMahon et al. | 128/200.18 |
| 5,533,501 | 7/1996 | Denyer | 128/203.12 |

FOREIGN PATENT DOCUMENTS

| | | |
|---|---|---|
| 471323 | 2/1992 | European Pat. Off. . |
| 587380 | 3/1994 | European Pat. Off. . |
| 627266 | 12/1994 | European Pat. Off. . |
| 653218 | 5/1995 | European Pat. Off. . |
| 4322111 | 1/1995 | Germany . |

*Primary Examiner*—John G. Weiss
*Assistant Examiner*—V. Srivastava
*Attorney, Agent, or Firm*—MacMillan, Sobanski & Todd, LLC

[57] ABSTRACT

A medicament nebulizer in which a liquid medicament is drawn through capillary flow along a bell shaped path to an annular medicament orifice. Pressurized atomization air is discharged from an orifice and is directed against a deflector which causes the air to flow with a swirling turbulence over one or more medicament orifices. The atomization air aspirates medicament from the medicament orifice and atomizes the medicament. The turbulent swirling flow of the atomization air decreases the average size of the droplets in the resulting aerosol. The flow path of the aerosol through an aerosol chamber to a mouthpiece may rapidly change directions to facilitate condensation of any large droplets in the aerosol. Alternately, a swirling or spiral flow direction may be imparted to the aerosol as it passes through the aerosol chamber to cause any larger droplets to contact and condense on the walls of the chamber.

18 Claims, 6 Drawing Sheets

NEBULIZER

TECHNICAL FIELD

The invention relates generally to nebulizers and more particularly to medicament nebulizers for producing a liquid medicament aerosol having a small droplet size for inhalation therapy.

BACKGROUND ART

Various types of nebulizers have been designed for generating a liquid medication aerosol for delivery to a patient's lungs. In designing a medicament nebulizer, a common goal is to produce an aerosol having as droplets which are very small and as uniform as possible. Only the small droplets will remain in suspension to penetrate deep into a patients lungs. Because of their mass and inertia, any larger size droplets inhaled by a patient will tend to collide with and collect on the walls of the respiratory tract before penetrating deep into the lungs. Generally, the medicament must penetrate deep into the lungs to produce the desired therapeutic effect. Medicament which never reaches the effective areas of the lungs is wasted and consequently increases the cost of the treatment.

As a patient inhales through a mouth piece in one common type of nebulizer, ambient air is drawn through a chamber to the patient. Pressurized air also is delivered to the chamber and is directed over a liquid orifice to aspirate and atomize liquid medicament, thereby forming an aerosol. Normally, the aerosol is mixed with the flow of ambient air which the patient inhales. However, the aerosol may be mixed with oxygen or with oxygen enriched air when required by the patient. Various techniques have been used to deliver the liquid to the orifice, to the make the liquid droplets in the aerosol as small as possible and to separate any larger droplets from the aerosol while the droplets remain in the nebulizer.

In one prior art nebulizer design, pressurized atomization air is discharged through an orifice and is deflected to flow over a fluid orifice to aspirate a fluid stream from the orifice and to atomize the fluid into small droplets as the fluid stream is drawn into the stream of atomization air. The droplets will have a range of sizes. The resulting aerosol is mixed with a larger volume flow of ambient air as it is drawn into the patient's lungs when the patient inhales. Various types of deflectors have been used to direct the atomization air over the fluid orifice to aspirate and atomize the fluid. In one nebulizer design, two fluid orifices are provided on diametrically opposite sides of an atomization air orifice. The atomization air is directed against a deflector bar which splits the air flow into two streams, one flowing over each orifice. In another nebulizer design, the atomization air is discharged from an orifice which is concentric with an annular fluid orifice. The atomization air is directed against a rounded or conical deflector to direct the air flow in a radial pattern over the annular fluid orifice. After the liquid is atomized, it is mixed with a larger volume flow of ambient air when the patient inhales. When the patient is not inhaling, the droplets in the aerosol condense on the interior walls of the nebulizer and flow back to the reservoir. Typically, the aerosol is directed either downwardly towards a fluid reservoir or radially outwardly towards the walls of the reservoir and then flows upwardly towards an aerosol outlet. When the aerosol is caused to follow a tortuous flow path in the nebulizer, the larger droplets tend to collide with and condense on the walls of the chamber and flow back to the fluid reservoir.

One problem with certain prior art nebulizer designs is that the fluid will flow to the fluid orifices for atomization only when the nebulizer is held in an upright orientation. As the atomizer is tilted, the fluid flow to the fluid orifice may decrease and the quantity of droplets generated may drop off and eventually cease, and the average size of the droplets may change. When a patient confined to a bed requires respiratory therapy using a nebulizer, it may be necessary to significantly tilt the nebulizer in order to administer the therapy. Also, sometimes younger children may not hold the nebulizer in an upright position while receiving therapy. Even when nebulizers have been designed to permit tilting during use, they often had a significant residual volume of medicament which could not be atomized by the tilted nebulizer.

Some nebulizers use capillary feed for delivering a flow of liquid from a reservoir to the liquid discharge orifice where the liquid is atomized. So long as a portion of the capillary flow passage is submerged in liquid in the reservoir, liquid will tend to flow to the liquid discharge orifice. In one prior art design, the reservoir has a rounded bottom which delivers the liquid to the lower end of a generally tubular capillary flow passage. However, tilting this nebulizer to any significant degree will interrupt liquid flow, since the inlet end of the capillary feed passage will no longer be submerged in the liquid. In another prior art design, the reservoir has a generally flat bottom extending to a circular side wall. A disk is spaced slightly from the bottom and from the side wall to form a disk shaped capillary fluid feed passage. Near the center of the reservoir, the disk shaped passage connects with a tubular shaped capillary fluid feed passage which leads to the liquid discharge orifice. This construction creates a long fluid feed passage with a 90° bend in the middle. In still another prior art design, an upwardly extending conical capillary passage extends from near a circular side wall of the reservoir to a fluid discharge orifice which surrounds an atomization air orifice. The conical capillary fluid feed passage has a disadvantage in that the upwardly extending conical center in the reservoir limits the capacity of the reservoir unless the size of the reservoir is increased.

Many of the prior art nebulizers are designed to be used only once or a few times and to then be thrown away. The nebulizer design may not lend itself to be easily cleaned so that the nebulizer can be reused.

DISCLOSURE OF INVENTION

The invention is directed to a liquid medicament nebulizer which is capable of operating both in an upright orientation and when tilted up to 90° from an upright orientation without loss of atomization and without significantly changing the average particle size. The nebulizer has a hollow generally tubular three section housing. A liquid medicament reservoir is formed in a lower housing section. The reservoir has a generally bell shaped lower surface which curves from a circular outer wall inwardly and upwardly toward a central axis. An atomization air discharge orifice is located axially on the apex of the lower surface. A complementary baffle fits over and is spaced from the lower surface to define a bell shaped capillary fluid feed passage which extends from adjacent the tubular outer wall to an annular fluid orifice which surrounds the atomization air orifice. The atomization air is directed against a deflector on the baffle which directs the air in an outwardly swirling direction over the fluid orifice in order to aspirate and atomize the fluid. The swirling action imparts turbulence to the atomization air which in turn improves atomization by breaking up larger fluid droplets into smaller droplets. Fins also may be provided on the baffle to impart a swirling action to the aerosol flow in the housing. The swirling or spiral flow of the aerosol helps in the collection of any larger fluid droplets on the walls of the housing where they return to the reservoir. The nebulizer delivers an aerosol to the patient in which the liquid droplets are smaller in average size and greater in quantity than those produced in prior art nebulizers.

In manufacturing the nebulizer, a three section housing is formed to include a reservoir section, a lower manifold section and an upper manifold section. The baffle is held in position in the reservoir section during use. The housing sections and baffle are easily separated to facilitate cleaning, allowing the nebulizer to be reused.

Accordingly, it is an object of the invention to provide an improved nebulizer for administering an aerosol to the lungs of a patient requiring respiratory therapy.

Other objects and advantages of the invention will become apparent from the following detailed description of the invention and the accompanying drawings.

BEST MODE FOR CARRYING OUT THE INVENTION

Figure 1:
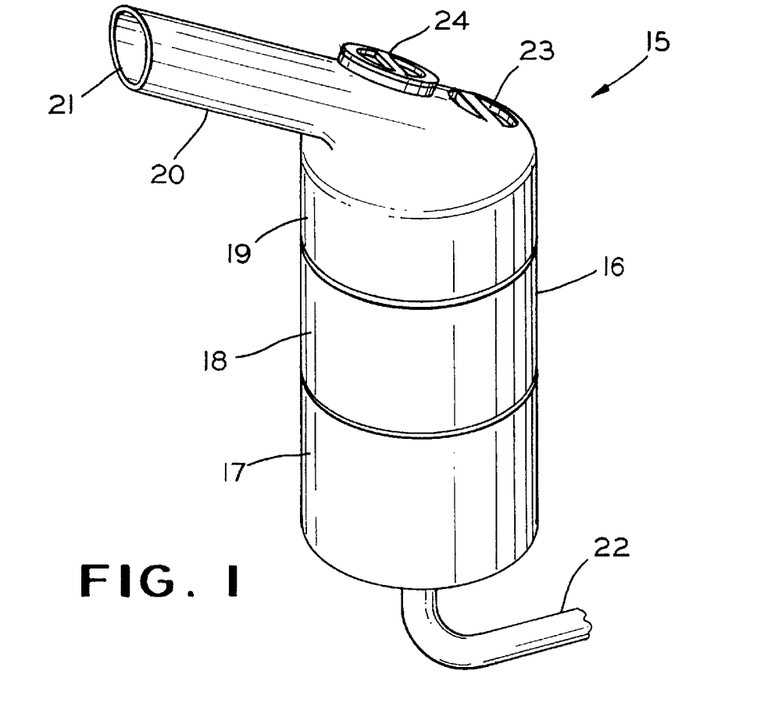
FIG. 1 is a perspective view of a nebulizer according to a preferred embodiment of the invention.

Referring now to FIG. 1 of the drawings, a nebulizer 15 is illustrated according to a preferred embodiment of the invention. The nebulizer 15 has a generally tubular housing 16 which is divided into a lower fluid reservoir section 17, a lower manifold section 18 and an upper manifold section 19. A tubular mouthpiece 20 angles to one side and in a slight upward direction on the upper manifold section 18. The mouthpiece 20 has an open free end 21 which is adapted to be inserted into a patient's mouth for administering a medicament aerosol to a patient as the patient breathes through the mouthpiece 20. A fragmentary portion of an air hose 22 is shown connected to the reservoir section 17. The air hose 22 is connected to a suitable source of pressurized gas (not shown), such as a conventional medical air compressor of the type designed for operating medical nebulizers. A flow of pressurized air from the hose 22 atomizes fluid medicament held in the reservoir section 17 into small droplets. When a patient inhales through the mouthpiece 20, ambient air is drawn through a check valve 23 on the upper manifold section 19, the air is mixed with the atomized medicament to form an aerosol and the aerosol is discharged through the open mouthpiece end 21 to the patient. When the patient exhales, the check vane 23 closes and the exhaled gas is discharged to the atmosphere through a check valve 24.

Internal details of the nebulizer 15 are shown in FIGS. 2–5. The reservoir section 17 has a generally tubular outer wall 25. An inner tubular wall 26 is spaced coaxially with the outer wall and the walls 25 and 26 are attached together at an upper end 27 of the inner wall 26. A generally bell shaped bottom 28 extends inwardly and upwardly from the inner wall 26 to form a fluid reservoir chamber 29 having a predetermined capacity. Preferably, the nebulizer 15 is designed to hold and operate with up to 9 cc of liquid medicament. If desired, medicament volume fill level marks (not shown) may be placed on the wall of the chamber 29 or on the outer wall 25 to show the volume of liquid in the reservoir chamber 29. A short tube 30 extends downwardly from the center of the bell shaped bottom 28. The tube 30 preferably has a slightly tapered exterior and is sized to receive an end 31 of the pressurized atomization air delivery tube 22. An axially positioned passage 32 extends through the tube 30 to an atomization air discharge orifice 33 located on an apex 34 of the bell shaped bottom 28.

Figure 2:
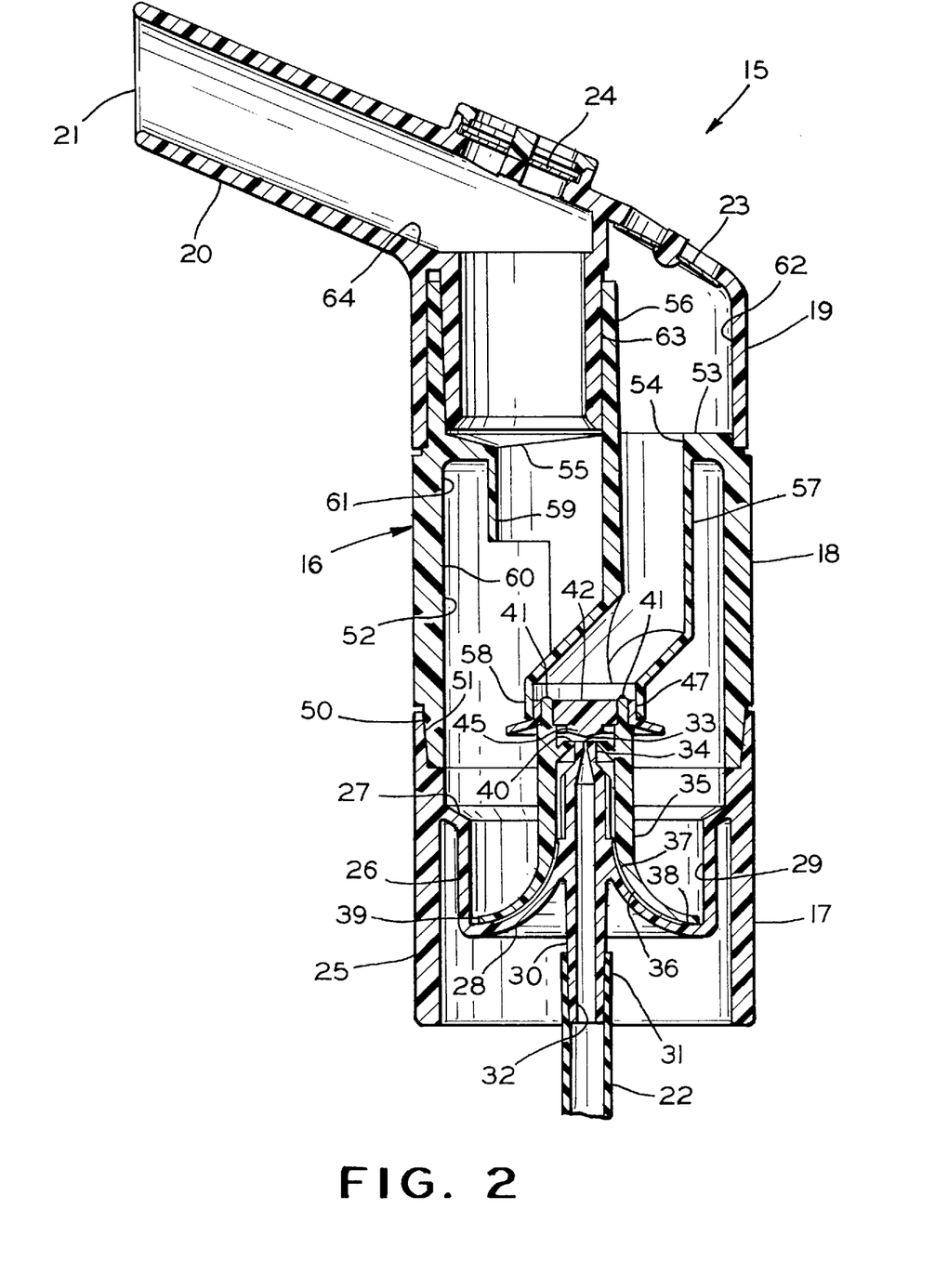
FIG. 2 is a side elevational cross sectional view of the nebulizer of FIG. 1.
Figures 3, 4:
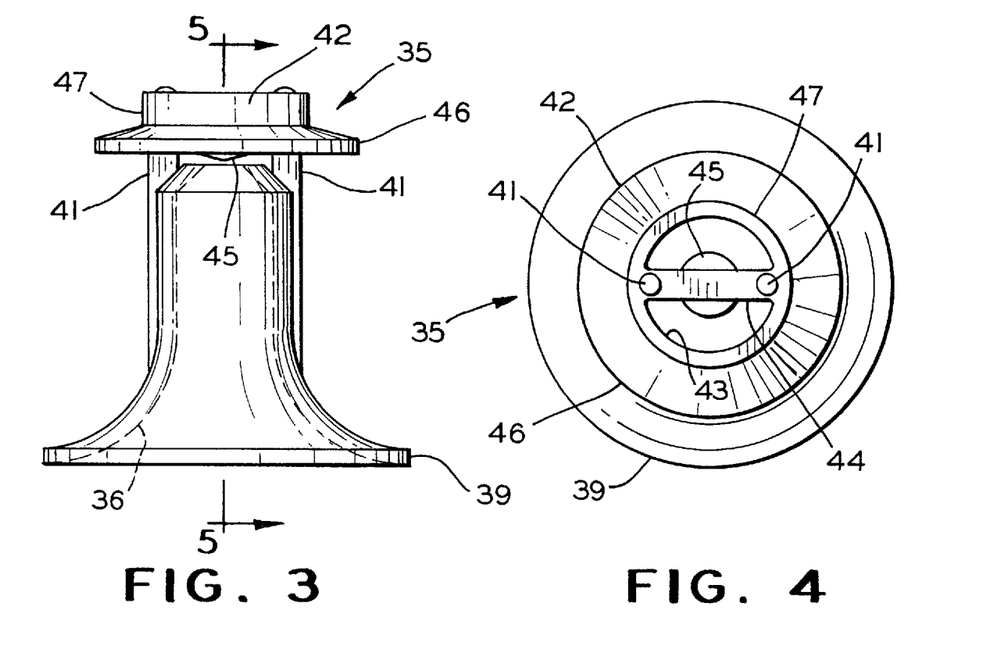
FIG. 3 is a is a side elevational view of a baffle for the nebulizer of FIG. 1.
FIG. 4 is a top plan view of the baffle of FIG. 3.
Figure 5:
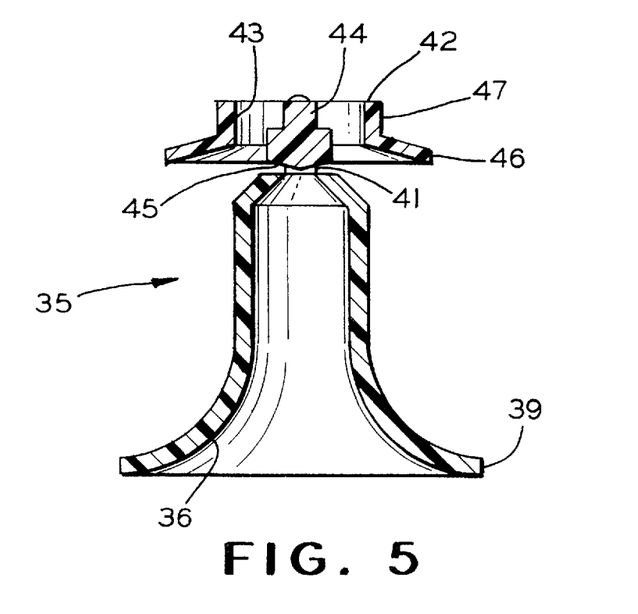
FIG. 5 is a cross sectional view of the baffle as taken along line 5—5 of FIG. 3.

A baffle 35 is sized to fit over the bell shaped reservoir bottom 28. The baffle 35 has a bell shaped lower surface 36 which is complementary to and slightly spaced from the reservoir bottom 28 to form a capillary fluid feed passage 37. A plurality of circumferentially spaced ridges 38 may be provided on the bottom 28 and/or on the baffle surface 36 for spacing the surface 36 from the bottom 28 to maintain a uniform circumferential thickness to the capillary fluid feed passage 37. The baffle 35 has an annular lower perimeter 39 which is slightly spaced from the wall 26 to form an annular inlet for the capillary fluid feed passage 37. The capillary fluid feed passage 37 extends to an annular fluid discharge orifice 40 which surrounds the atomization air discharge orifice 33. By providing a bell shape to the bottom of the reservoir chamber 29 and having the annular inlet to the capillary fluid feed passage, the residual liquid which will not be atomized is minimized and the volume of liquid which the reservoir will hold is increased over a nebulizer having a conical shaped reservoir bottom. Consequently, the bell shaped bottom provides the advantages of a conical capillary feed passage without the fluid capacity decrease resulting from a conically shaped bottom.

Two diametrically opposing parallel pins 41 secure an annular top 42 on the baffle 35. The top 42 is spaced above the atomization air orifice 33 and the fluid discharge orifice 40. The top 42 has a central opening 43 which is bridged by a rod 44. An atomization air deflector 45 is mounted on the rod 43 for deflecting the atomization air from the orifice 33 in a generally spiral direction over the fluid discharge orifice 40, as will be described in greater detail below. The top 42 has a skirt 46 which directs the atomized particles in an outwardly and downwardly direction. Above the skirt 46, the top 42 has a cylindrical outer wall 47.

The lower manifold section 18 of the housing 16 is releasably secured to the reservoir section 17. A tapered lower end 50 on the lower manifold section 18 may be pressed into a complementary interior tapered rim 51 on the reservoir section for holding the sections 17 and 18 together by friction. Alternately, a conventional bayonet type connection (not shown) or a threaded connection (not shown) may be provided between the sections 17 and 18 for releasably securing the sections together. The lower manifold section 18 is tubular shaped and has an interior aerosol chamber 52 which connects with the reservoir chamber 29. An upper end 53 of the housing section 18 has an air inlet opening 54 and an aerosol outlet opening 55 A tube 56 surrounds the aerosol outlet opening 55 and projects from the upper end 53 of the lower manifold section 18. A tube 57 extends from the air inlet opening 54 downwardly into the chamber 52 to an axially located open end 58. When the lower manifold section 18 is secured to the reservoir section 17, the tube end 58 receives the cylindrical wall 47 on the baffle top 42.

A downwardly directed flange 59 surrounds the aerosol outlet opening 55 and extends from the upper end 53 into the aerosol chamber 52. The flange 59 is spaced from an outer wall 60 of the lower manifold section 18. A downwardly opening recess 61 is formed between the outer wall 60, the flange 59 and the end 53. Preferably, the recess 61 has a volume at least as large as the maximum volume of liquid placed in the reservoir chamber 29. In the event that the nebulizer 15 is inverted, any liquid in the reservoir chamber 29 will flow into the recess 61 and will not leak from the open mouthpiece end 21.

The upper manifold section 19 defines two separate chambers. The inhale check valve 23 communicates with an ambient air chamber 62 which in turn connects with the opening 54. A tube 63 in the upper manifold section 19 slides into and frictionally engages the tube 56 which projects from the lower manifold section 18 to hold the manifold sections 18 and 19 together. The interiors of the tube 63 and the mouthpiece 20 form an aerosol outlet chamber 64. The exhale check valve 24 is connected to exhaust air from the aerosol outlet chamber 64 when a patient exhales into the mouthpiece 20. Since the inhale check valve 23 will close when the patient exhales into the mouthpiece 20, the exhaled gas cannot enter the aerosol chamber 52.

In operation, a desired quantity of a liquid medicament is placed in the reservoir chamber 29 and the housing sections 17, 18 and 19 are connected together. A medical air compressor (not shown) is connected through the hose 22 to supply pressurized air to the nebulizer 15 for atomizing the medicament. The atomization air is discharged from the orifice 33 and is directed in a generally radial direction over the annular fluid discharge orifice 40. Fluid flows from the reservoir chamber 29 to adjacent the fluid discharge orifice 40 through capillary action. The air flow over the fluid discharge orifice 40 aspirates the fluid from the orifice 40 and atomizes the fluid into small droplets. The atomization air will be exhausted either through the open mouthpiece end 21 or through the check valve 24 when the mouthpiece end 21 is blocked. The flow of atomization air from the orifice 33 is quite low. Until a patient breathes on the mouthpiece 20, the droplets will remain in and eventually condense on the walls of the aerosol chamber 52. The condensed droplets flow back into the reservoir chamber 29 and subsequently will be atomized again.

When a patient inserts the mouthpiece 20 into his or her mouth and inhales, ambient air is drawn through the check valve 23. The air flows through the chamber 62 and the tube 57 to the baffle opening 43. The air is drawn downwardly through the baffle opening 43 and mixes with the atomized fluid droplets to form an aerosol which flows radially outwardly and downwardly, as directed by the skirt 46. The aerosol flow then changes directions and is drawn upwardly through the chamber 52 and through the mouthpiece chamber 64 to the patient's mouth. When the aerosol flow changes directions in the chamber 52, larger particles are more resistant to change their flow direction because of inertia and tend to collide with and condense on the walls of the chamber 52.

Figure 6:
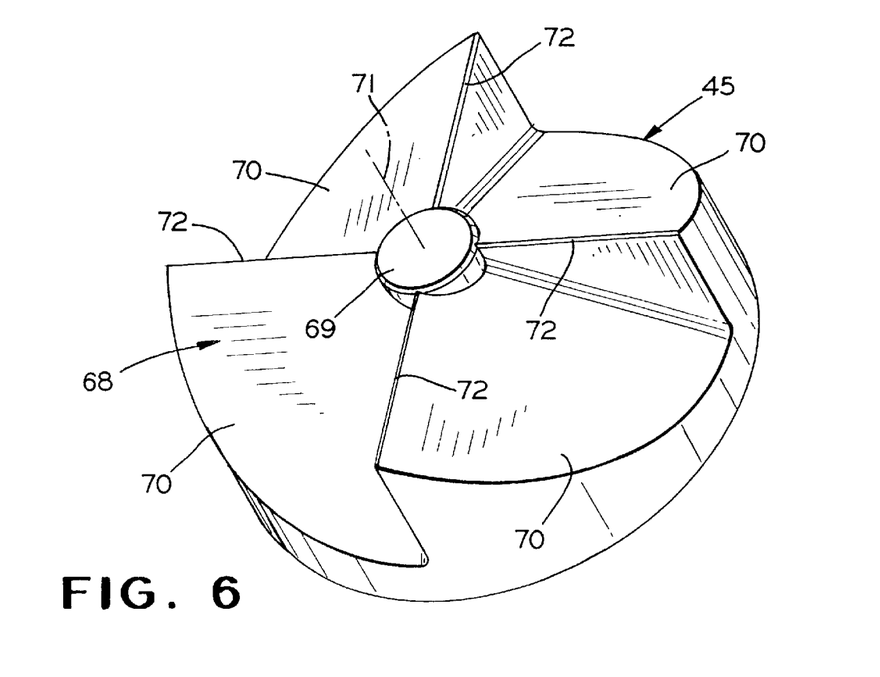
FIG. 6 is an enlarged perspective view showing details of the bottom surface of one embodiment of an atomization air deflector for the baffle of FIG. 3.

According to one feature of the invention, the atomization air deflector 45 is designed to impart a swirling or spiral flow action to the deflected air. The increased turbulence in the swirling atomization air enhances the breakup of the fluid into smaller droplets as it is atomized. FIG. 6 is an enlarged perspective view showing details of an atomization air deflecting surface 68 on the deflector 45. The air deflecting surface 68 has a flat center 69 against which the center of the pattern of air discharged from the orifice 33 (FIG. 2) is directed. When the air impinges against the flat surface 69, a pressure buildup causes the air to flow radially outwardly and over the fluid discharge orifice 40 (FIG. 2). As the air flows outwardly, it expands and its pressure decreases. A plurality of inclined, stepped, circumferentially spaced, planar surfaces 70 surround the center 69, with 4 such surfaces 70 illustrated. Each of the surfaces 70 is inclined at the same angle relative to a center axis 71 which is perpendicular to the flat surface 69 and each surface 70 has a radial leading edge 72. The stepped surfaces 70 are angled to impart a swirling turbulence to the expanding, outwardly flowing air. The swirling turbulence tends to break larger fluid droplets down into smaller droplets, thus providing more small droplets and reducing the average particle size in the aerosol.

Figure 7:
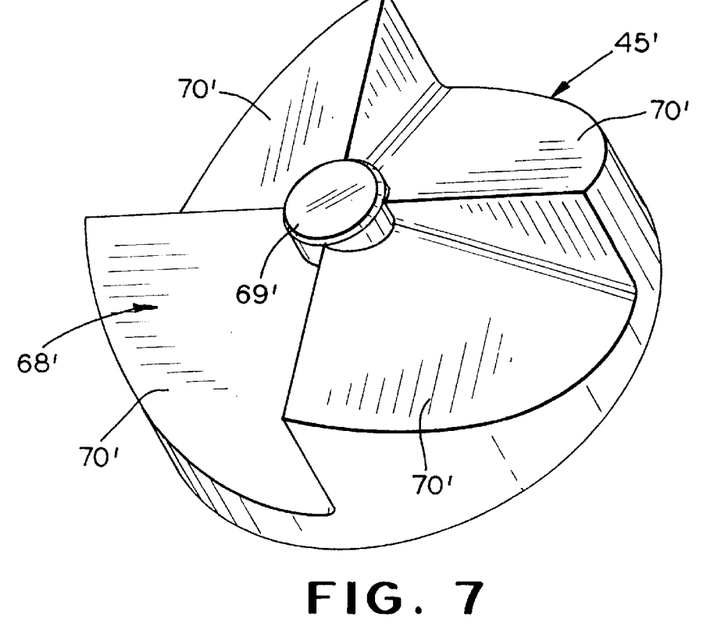
FIG. 7 is an enlarged perspective view showing details of the bottom surface of a modified embodiment of an atomization air deflector for the baffle of FIG. 3.

FIG. 7 shows an enlarged perspective view of an air deflecting surface 68' on a modified air deflector 45'. The deflecting surface 68' has a small rounded center 69' against which the center of the atomization air jet from the orifice 33 is directed. The rounded surface 69' deflects the atomization air in a radially outwardly directed pattern. Again, circumferentially spaced stepped surfaces 70' impart a swirling turbulence to the expanding flow of atomization air to facilitate breaking the fluid particles into small droplets.

Figure 8:
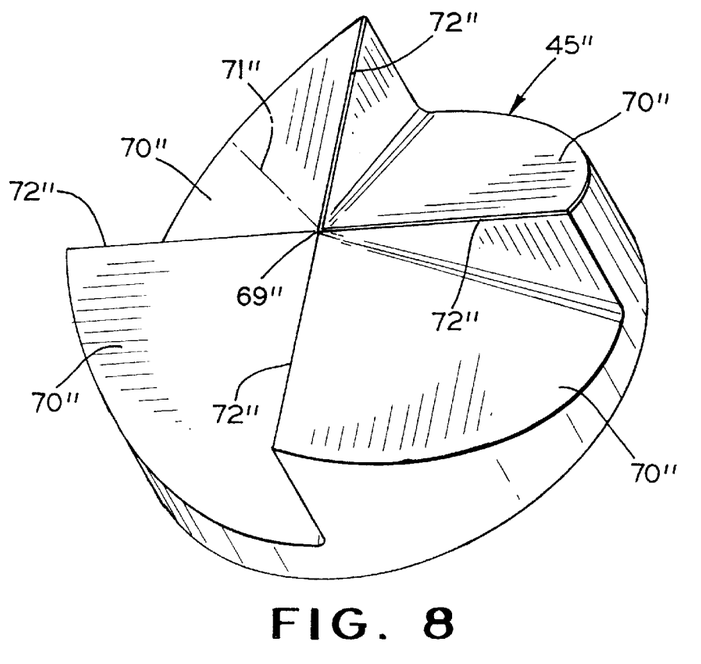
FIG. 8 is an enlarged perspective view showing details of the bottom surface of a further modified embodiment of an atomization air deflector for the baffle of FIG. 3.

FIG. 8 shows still a third embodiment of an air deflector 45". A plurality of inclined, stepped, circumferentially spaced, planar surfaces 70" converge at a center point 69" against which the jet of atomization air is impinged. Each of the planar surfaces 70" has a leading edge 72" which extends radially from a central axis 71". Each surface 70" is inclined relative to the axis 71". The surfaces 70" deflect the air in a spiral direction to impart a swirling turbulence to the expanding flow of atomization air.

Although the surface areas 70, 70' and 70" on the air deflectors of FIGS. 6–8 are illustrated as being flat, it should be appreciated that the surface areas may be curved areas, such as by providing a hollow or scoop shape to each surface area. The important feature is that the faces be oriented and shaped to impart a generally spiral or swirling turbulent flow to the expanding atomization air. The turbulent spiral flow of atomization air facilitates breaking the droplets down into smaller droplets. When the patient is not inhaling into the mouthpiece 20, the swirling flow also facilitates the condensation of the droplets on the walls of the chamber 52, since the flow of atomization air in the chamber 52 will not be affected by a large volume flow of ambient air.

Figure 9:
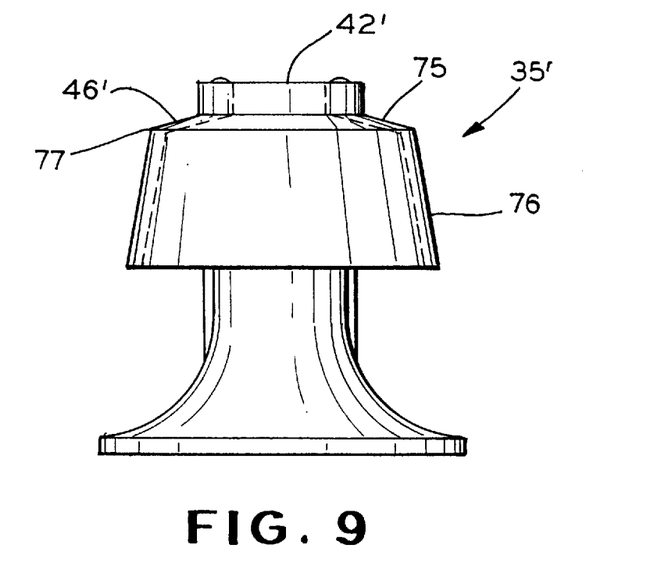
FIG. 9 is a side elevational view of a modified embodiment of a baffle for the nebulizer of FIG. 1.

The baffle 35 also may be modified to enhance the condensation of any remaining larger droplets in the aerosol before they leave the chamber 52. FIG. 9 shows a modified baffle 35'. The baffle 35' is of a similar construction to the baffle 35 of FIGS. 3–5, except for the configuration of a skirt 46' on a top 42'. The skirt 46' has an inner annular section 75 which flares outwardly and slightly downwardly. An outer skirt section 76 extends from a perimeter 77 of the skirt section 75 in a downwardly and slightly outwardly direction. When the baffle 35' is placed in the nebulizer 15 of FIGS. 1 and 2, the skirt 35' directs the aerosol in a downward direction towards the reservoir chamber 29. The aerosol must then reverse flow directions to flow towards the aerosol outlet chamber 64. By increasing the flow direction change, there is a greater tendency for any large particles in the aerosol to continue moving in a straight path and to strike either the surface of fluid in the reservoir chamber 29 or the walls of the aerosol chamber 52 before reaching the aerosol outlet chamber 64 and the patient.

Figure 10:
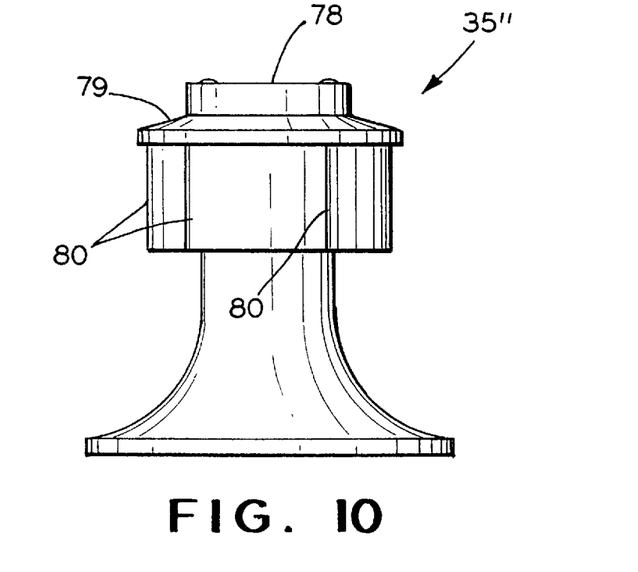
FIG. 10 is a side elevational view of a further modified embodiment of a baffle for the nebulizer of FIG. 1.
Figure 11:
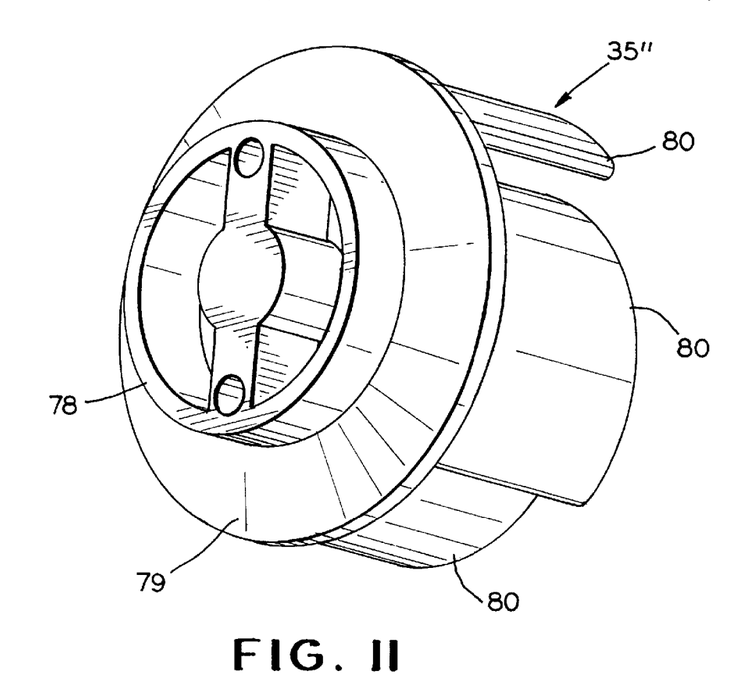
FIG. 11 is a top perspective view of the top section of the baffle of FIG. 10.
Figure 12:
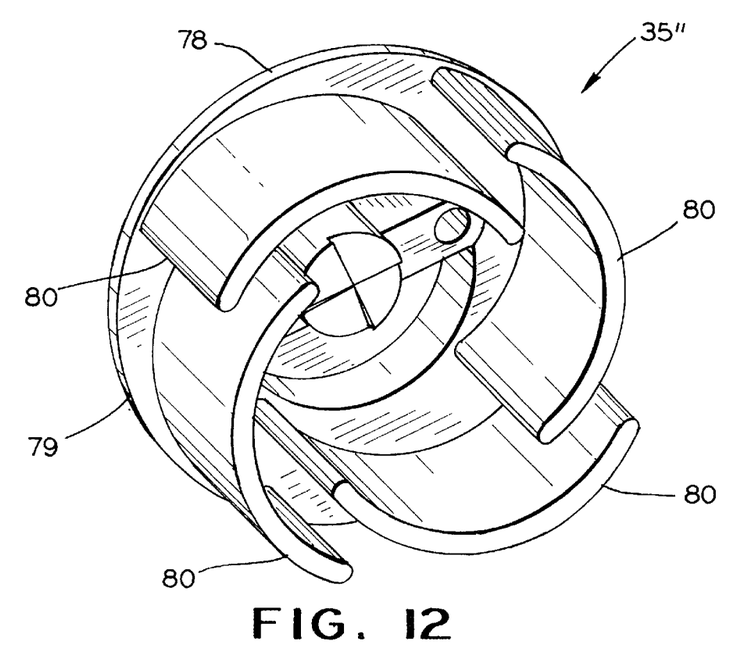
FIG. 12 is a bottom perspective view of the top section of the baffle of FIG. 10.

FIGS. 10–12 show details of a further modified baffle 35". The baffle 35" has a top 78 which includes an outwardly and slightly downwardly directed skirt 79. A plurality of fins 80 extend from the skirt 79. Although the fins 80 may be flat, they preferably are each in the form of an arcuate or spiral segment, as shown. The fins 80 are circumferentially spaced around the skirt 79. The skirt 79 directs the aerosol in a slightly downwardly direction and the fins 80 are arranged to impart either a clockwise or a counterclockwise swirling action to the aerosol as it flows outwardly and upwardly in the chamber 52 when the baffle 35" is used in the nebulizer 15 of FIGS. 1 and 2 and a patient inhales on the mouthpiece end 21. The swirling action causes any larger droplets in the aerosol to contact and condense on the walls of the chamber 52 through inertial separation, thereby reducing the average droplet size in the aerosol. Although the baffle 35" may have a conventional air deflector at its center, it preferably has a stepped air deflector surface 81 which deflects the air in the same direction as the fins 80. Thus, the stepped air deflector surface 81 and the fins 80 cooperate in increasing the swirling action of the aerosol to increase the effectiveness of the inertial separation of any larger droplets.

The goals of the invention are twofold. First, it is desired to produce a greater number of small droplets and fewer large droplets in the aerosol produced by the nebulizer. By using an atomization air deflector which imparts high turbulence and a swirling action to the atomization air in the atomization region, the average size of the droplets is decreased. In other words, the same amount of atomized fluid will produce more small droplets and fewer large droplets. Second, it is desired to more effectively remove any large droplets from the aerosol. The removal of the larger droplets is enhanced either by increasing the flow direction change as the aerosol flows to the patient or by imparting a spiral flow direction to the aerosol so that the larger particles are driven against and condense on the walls of the aerosol chamber. The nebulizer 15 also has an advantage over many prior art nebulizers in that it is easily disassembled for cleaning, thus permitting reuse of the nebulizer.

In the preferred embodiment of the nebulizer 15, the fluid orifice 40 is an annular orifice which surrounds the atomization air orifice 33. It should be appreciated that the annular fluid orifice 40 may be replaced with a plurality of orifices which are uniformly spaced from the atomization air orifice 33.

It will be appreciated that various modifications and changes may be made to the above described preferred embodiments of a nebulizer without departing from the scope of the following claims.

We claim:

1. A medicament nebulizer comprising a reservoir chamber adapted to receive a volume of medicament for atomization, said reservoir chamber having a circular outer wall and a bell shaped bottom, said bottom curving inwardly and upwardly to an apex, an atomization air discharge orifice at said apex, a baffle positioned over said chamber bottom, said baffle having a curved surface spaced from said bottom to define a bell shaped capillary medicament feed passage having an annular inlet adjacent said circular outer wall and terminating at an annular orifice surrounding said atomization air discharge orifice, and a deflector positioned in the path of air discharged from said atomization air discharge orifice, said deflector directing air over said annular medicament orifice for aspirating and atomizing the medicament, wherein said deflector has a surface adapted to direct the atomization air, said deflector surface having a center axis and having a plurality of circumferentially spaced surface areas adapted to impart a turbulent swirling action to atomization air directed over said annular medicament orifice.

2. A medicament nebulizer, as set forth in claim 1, and wherein said circumferentially spaced surface areas are circumferentially stepped around said axis and are inclined relative to said axis.

3. A medicament nebulizer, as set forth in claim 2, and wherein each of said surfaces is inclined at the same angle relative to said axis.

4. A medicament nebulizer, as set forth in claim 3, and wherein said deflector surface further includes a center surface area separate from said stepped surface areas and adapted for impingement by a flow of air from said atomization air discharge orifice.

5. A medicament nebulizer, as set forth in claim 4, and wherein said center surface area is a flat surface extending perpendicular to said axis.

6. medicament nebulizer, as set forth in claim 4, and wherein said center surface area is rounded.

7. A medicament nebulizer, as set forth in claim 1, and further including an aerosol chamber for receiving the atomized medicament, and means for imparting a spiral flow direction to a flow of atomized medicament in said aerosol chamber.

8. A medicament nebulizer, as set forth in claim 7, and wherein said means for imparting a spiral flow direction to atomized medicament includes a plurality of fins arranged to impart such spiral flow direction to a flow of atomized medicament.

9. In a medicament nebulizer having an atomization air discharge orifice which directs a flow of air to impinge against a deflector having a deflector surface which deflects such air to flow over a medicament orifice for aspirating and atomizing medicament from said medicament orifice, an improved deflector surface comprising a plurality of circumferentially spaced surface areas surrounding a center axis, and wherein said surface areas are adapted to impart a turbulent swirling action to deflected atomization air.

10. An improved deflector surface for a nebulizer, as set forth in claim 9, and wherein each of said surface areas is an inclined step, and wherein said surface areas are inclined at the same angle relative to said axis.

11. An improved deflector surface for a nebulizer, as set forth in claim 10, and wherein each of said surface areas is flat.

12. An improved deflector surface for a nebulizer, as set forth in claim 11, and wherein each of said surface areas has a radially directed edge.

13. An improved deflector surface for a nebulizer, as set forth in claim 9, and wherein each of said surface areas is a flat area inclined relative to said axis and has a radially directed edge.

14. An improved deflector surface for a nebulizer, as set forth in claim 9, and further including a center surface area separate from said circumferentially spaced surface areas located at the center of said deflector for impingement by a flow of air from the atomization air discharge orifice.

15. An improved deflector surface for a nebulizer, as set forth in claim 14 and wherein said center surface area is a flat surface extending perpendicular to the center axis.

16. An improved deflector surface for a nebulizer, as set forth in claim 13, and wherein said center surface area is rounded.

17. In a nebulizer having an aerosol chamber and means located in a central region of the aerosol chamber for generating an aerosol which initially flows in a generally radial direction, the improvement comprising a baffle having a plurality of circumferentially spaced fins surrounding the aerosol generating means and adapted to impart a swirling action to the aerosol flow in the aerosol chamber.

18. A baffle for a nebulizer, as set forth in claim 17, and wherein each of said fins has a spiral shape.

* * * * *